US010274135B2

(12) United States Patent
Kiliszewski et al.

(10) Patent No.: US 10,274,135 B2
(45) Date of Patent: Apr. 30, 2019

(54) TRANSILLUMINATION LIGHT SOURCE

(71) Applicant: Neotech Products LLC, Valencia, CA (US)

(72) Inventors: Larry Kiliszewski, The Woodlands, TX (US); Ketan Mehta, Sugar Land, TX (US); Reuben Bromiker, Zur Hadassa (IL)

(73) Assignee: Neotech Products LLC, Valencia, CA (US)

( * ) Notice: Subject to any disclaimer, the term of this patent is extended or adjusted under 35 U.S.C. 154(b) by 0 days.

(21) Appl. No.: 15/631,182

(22) Filed: Jun. 23, 2017

(65) Prior Publication Data

US 2018/0045378 A1    Feb. 15, 2018

Related U.S. Application Data

(60) Provisional application No. 62/373,208, filed on Aug. 10, 2016.

(51) Int. Cl.
*F21V 3/02*    (2006.01)
*F21K 9/20*    (2016.01)
(Continued)

(52) U.S. Cl.
CPC .............. *F21K 9/20* (2016.08); *A61B 5/0059* (2013.01); *A61B 5/150748* (2013.01); *A61B 5/489* (2013.01); *F21V 3/02* (2013.01); *A61B 5/6823* (2013.01); *A61B 5/6826* (2013.01); *A61B 5/7475* (2013.01); *A61B 2560/0214* (2013.01); *A61B 2560/0431* (2013.01); *F21Y 2101/00* (2013.01); *F21Y 2115/10* (2016.08)

(58) Field of Classification Search
CPC .......... F21K 9/20; F21V 3/02; F21Y 2101/00; F21Y 2115/10
See application file for complete search history.

(56) References Cited

U.S. PATENT DOCUMENTS 5,594,433 A * 1/1997 Terlep .................... B60Q 7/00
340/473
6,056,692 A     5/2000 Schwartz
(Continued)

FOREIGN PATENT DOCUMENTS

EP    3086711 A1    11/2016

OTHER PUBLICATIONS

Yusoff, Suhaimi et al., Review on Vein Enhancement Methods for Biometric System., Internatoinal Journal of Research in Engineering and Technology, Apr. 2015, pp. 833-841, vol. 4, Issue 4, Malaysia.

*Primary Examiner* — Donald L Raleigh
(74) *Attorney, Agent, or Firm* — Kelly & Kelley, LLP (57) ABSTRACT

A handheld and portable transillumination light source device allows for visualizing and locating vasculature and other subcutaneous structures of the body. One or more forward and upward facing LEDs are provided to project light out of a forward or upper surface of the device respectfully. The LEDs may vary as to the wavelengths of light the LEDs emit. A control button allows a user to switch the device between various modes of lighting, as well as, to adjust the intensity of the LEDs. Alternatively, these buttons may be split into separate power and intensity buttons. Touch sensors or a touch strip may also be provided to adjust the intensity of the LEDs.

20 Claims, 10 Drawing Sheets

US 10,274,135 B2

Page 2

(51) Int. Cl.
*A61B 5/00* (2006.01)
*A61B 5/15* (2006.01)
*F21Y 115/10* (2016.01)
*F21Y 101/00* (2016.01)

(56) References Cited

U.S. PATENT DOCUMENTS

| | | | |
|---|---|---|---|
| 6,178,340 B1 | 1/2001 | Svetliza | |
| 6,463,309 B1 | 10/2002 | Ilia | |
| 6,556,854 B1 | 4/2003 | Sato et al. | |
| 6,959,999 B2* | 11/2005 | Lee | F21L 13/06 |
| | | | 362/183 |
| 7,352,339 B2 | 4/2008 | Morgan et al. | |
| 7,532,746 B2 | 5/2009 | Marcotte et al. | |
| 7,772,786 B2 | 8/2010 | Hosoda et al. | |
| 7,841,751 B2 | 11/2010 | Mulani | |
| 8,463,364 B2 | 6/2013 | Wood et al. | |
| 8,838,210 B2 | 9/2014 | Wood et al. | |
| 8,954,134 B2 | 2/2015 | Imam | |
| 9,705,597 B2* | 7/2017 | Latham | H04B 10/116 |
| 2004/0073278 A1 | 4/2004 | Pachys | |
| 2004/0171923 A1 | 9/2004 | Kalafut et al. | |
| 2004/0264187 A1* | 12/2004 | Vanderschuit | F21S 6/005 |
| | | | 362/235 |
| 2005/0168980 A1 | 8/2005 | Dryden et al. | |
| 2005/0215875 A1 | 9/2005 | Khou | |
| 2007/0247840 A1* | 10/2007 | Ham | F21S 9/022 |
| | | | 362/227 |
| 2008/0015663 A1 | 1/2008 | Mullani | |
| 2008/0039715 A1 | 2/2008 | Wilson et al. | |
| 2008/0192467 A1* | 8/2008 | Rizkin | F21V 5/046 |
| | | | 362/245 |
| 2009/0018414 A1 | 1/2009 | Toofan | |
| 2013/0020462 A1* | 1/2013 | Kim | F21K 9/13 |
| | | | 250/205 |
| 2014/0133150 A1* | 5/2014 | Pardikes | F21V 21/005 |
| | | | 362/249.02 |
| 2014/0168955 A1* | 6/2014 | Gershaw | F21S 8/026 |
| | | | 362/147 |
| 2014/0350408 A1 | 11/2014 | Goldman et al. | |
| 2015/0051460 A1 | 2/2015 | Saxena et al. | |
| 2016/0197502 A1* | 7/2016 | Waters | F21L 4/085 |
| | | | 340/636.1 |
| 2016/0242649 A1 | 8/2016 | Mullani | |

* cited by examiner

TRANSILLUMINATION LIGHT SOURCE

RELATED APPLICATION

This application claims the benefit of U.S. Provisional Application No. 62/373,208, filed on Aug. 10, 2016.

BACKGROUND OF THE INVENTION

The present invention generally relates to an imaging device. More specifically, the present invention is directed to a handheld transillumination light source for locating and visualizing veins, arteries, and other subcutaneous structures of the body.

One of the first steps that a clinician takes in examining and diagnosing a patient is to visualize and palpate the area or structure of the patient's body to be examined. For example, when a clinician needs to perform an intravenous injection or extraction, he or she will often look for a vein seen from the surface of the skin or palpate the area to try and feel where a vein is located. If a vein cannot be seen or felt, a clinician may resort to using a tourniquet or asking the patient to pump his or her fist in hopes that veins will dilate and become visible. While this technique may be helpful in some instances, it still can be very difficult for a clinician to visualize and locate veins in patients with less prominent veins such as neonates, pediatric patients, obese patients, older adults, and patients with low blood pressure.

In these cases, transillumination has been a popular technique to assist the clinician in better visualizing and locating a patient's veins. Transillumination is a well-known imaging technique in which a sample is illuminated by the transmission of light through the sample. A clinician may use transillumination to illuminate a patient's arm, or other part of the patient's body from which fluid is to be injected or extracted. Because not as much light will penetrate through the patient's vasculature, the vasculature will appear darker and a clinician will have a visual of the patient's veins when inserting a needle for fluid injection or extraction.

A number of devices have been developed to allow a clinician to use the transillumination technique to visualize and locate the vasculature or any other subcutaneous structure in a patient. For example, U.S. Patent Application Publication No. 2005/0168980 to Dryden et al. discloses using one or more LEDs with predominant wavelengths between 600 and 640 nm. The LEDs are housed in a handheld vein locator device. However, the Dryden does not teach a transillumination device in which a clinician may use LEDs with differing wavelengths. Being able to use different wavelengths of light would be advantageous because different subcutaneous structures of the body absorb differing wavelengths of light. When light is absorbed by a structure, it will appear dark when compared to the rest of the tissue when using the transillumination technique. Thus, being able to switch between different wavelengths of light would enable a clinician to better visualize the associated subcutaneous structures.

U.S. Pat. Nos. 8,463,364 and 8,838,210 to Wood et al. both disclose similar vein locator devices. These devices scan a portion of a patient's body with ultraviolet and infrared light in order to produce a signal which is read by the device. The signal is processed through an algorithm in order to produce an image of the vasculature of the patient which is projected onto the skin of the patient. These devices do not allow a clinician to visualize the actual vasculature of a patient, but only images of the patient's vasculature projected onto the patient's skin. Furthermore, these devices don't allow a clinician to visualize other subcutaneous structures.

Thus, it would be advantageous to develop a transillumination device which is cheap and easy to manufacture, portable, allows a clinician to choose from different wavelengths of light, and allows a clinician to adjust the brightness intensity of device. The present invention fulfills these needs and provides other related advantages.

SUMMARY OF THE INVENTION

The present invention is directed to a transillumination light source having a housing with a top longitudinal surface, a bottom longitudinal surface, and a front lateral surface. The bottom longitudinal surface has a generally flat portion configured to rest the housing on a flat work surface. The top longitudinal surface is generally opposite the bottom longitudinal surface and has a first translucent light cover. The front lateral surface is oriented generally perpendicular to the bottom longitudinal surface and has a second translucent light cover.

A circuit board is contained within the housing. The circuit board carries a power supply, an LED driver, and a control button. The power supply, LED driver, and control button are all operationally connected to each other. A plurality of upward facing LEDs are disposed on the circuit board. The upward facing LEDs are operationally connected to the LED driver and configured so as to direct illumination through the first translucent light cover. A plurality of forward facing LEDs are also disposed on the circuit board. The forward facing LEDs are operationally connected to the LED driver and configured so as to direct illumination through the second translucent light cover.

The plurality of upward facing LEDS preferably includes two white LEDs and two red LEDs. The plurality of forward facing LEDs preferably includes four white LEDs. The control button preferably has an operational setting configured to operate the LED driver to illuminate only the two white LEDs in the plurality of upward facing LEDs, only the two red LEDs in the plurality of upward facing LEDs, or only the four white LEDs in the plurality of forward facing LEDs. The control button may also have an intensity setting configured to regulate a brightness of LEDs illuminated by the LED driver.

The housing preferably has a connection port that is operationally connected to the power supply. The transillumination light source may be configured to be powered from an external source through the connection port. The power supply may be a battery enclosed behind a battery cover on the housing. The battery is preferably a rechargeable battery configured to be recharged through the connection port on the housing, which port is operationally connected to the rechargeable battery.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE INVENTION

As shown in the drawings, the present invention is directed to a handheld transillumination light source 30 for use in locating and visualizing veins, arteries, and other subcutaneous structures of a patient's body. Generally, the transillumination light source 30 assists a clinician in locating and visualizing veins and arteries so that the clinician may more easily perform fluid extraction or fluid insertion procedures. Furthermore, the transillumination light source 30 may also be useful in helping the clinician visualize other subcutaneous structures of the body for examination and diagnostic purposes.

FIGS. 1, 1A, 1B, and 1C show the external configuration of a preferred embodiment of the transillumination device 30. FIGS. 2, 3, 4, and 5 show the internal structure of the device 30 in various exploded and cut-away views.

Figure 1:
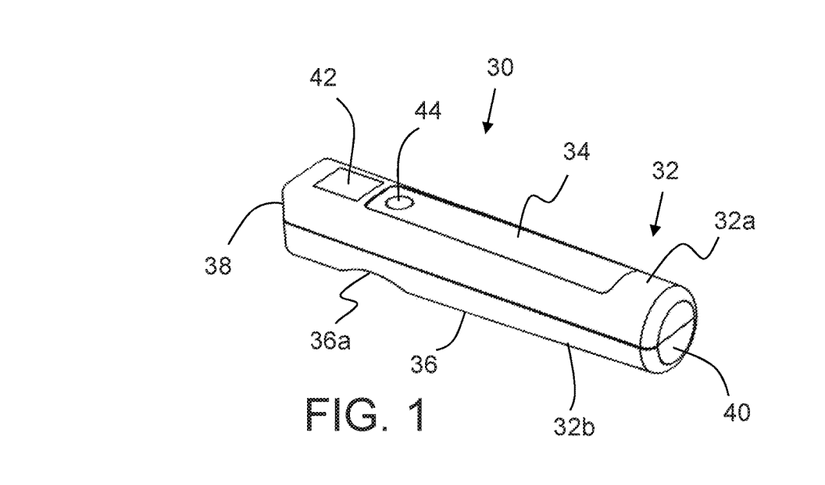
FIG. 1 is a perspective view of a transillumination device of the present invention.
Figure 1A:
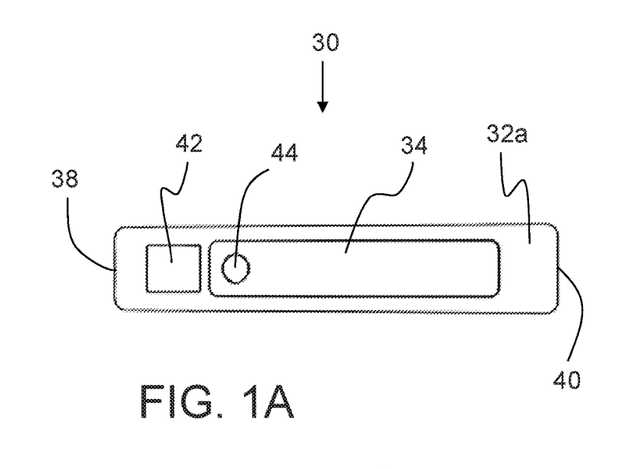
FIG. 1A is a top view of a transillumination device of the present invention.
Figure 2:
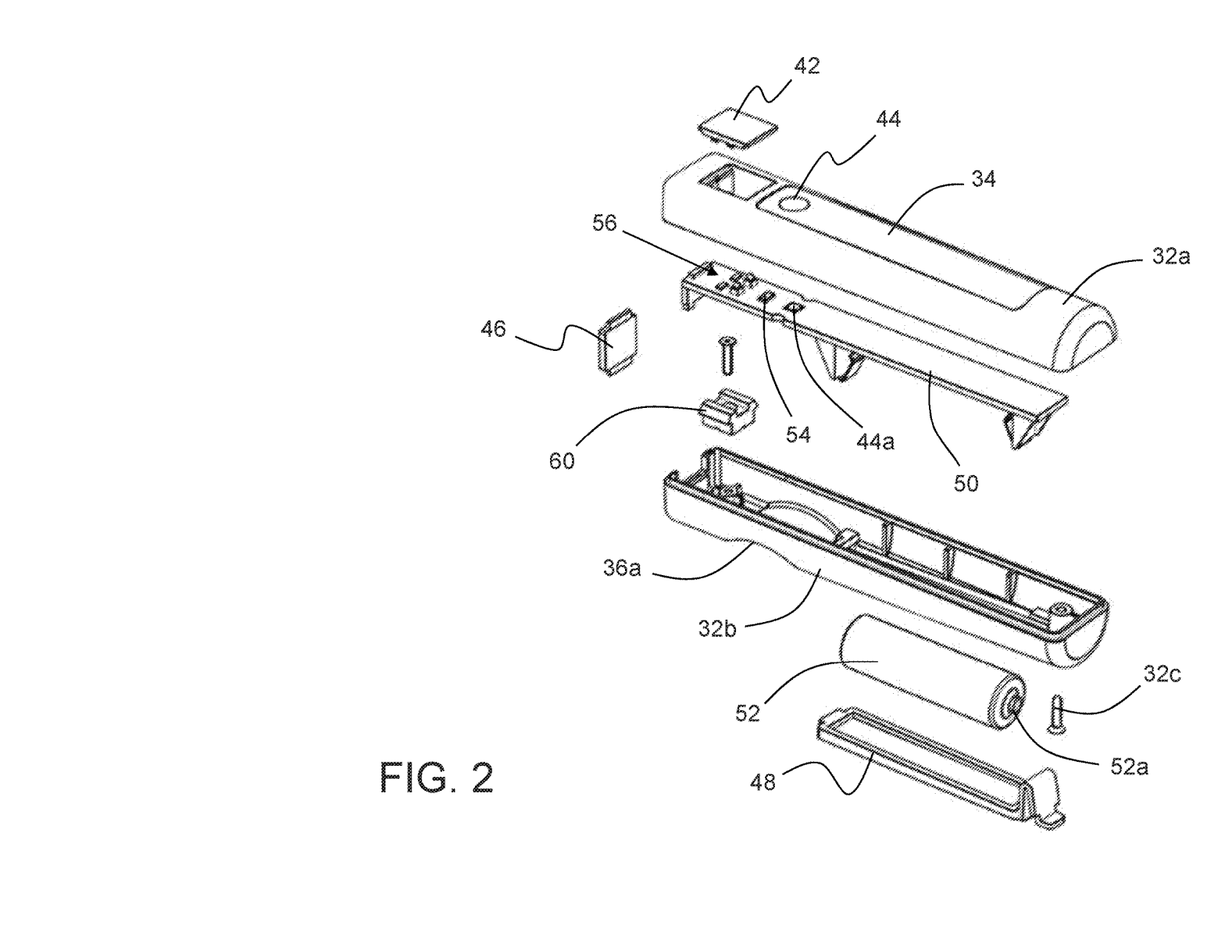
FIG. 2 is an exploded perspective view of a transillumination device of the present invention having a first preferred power supply.
Figure 3:
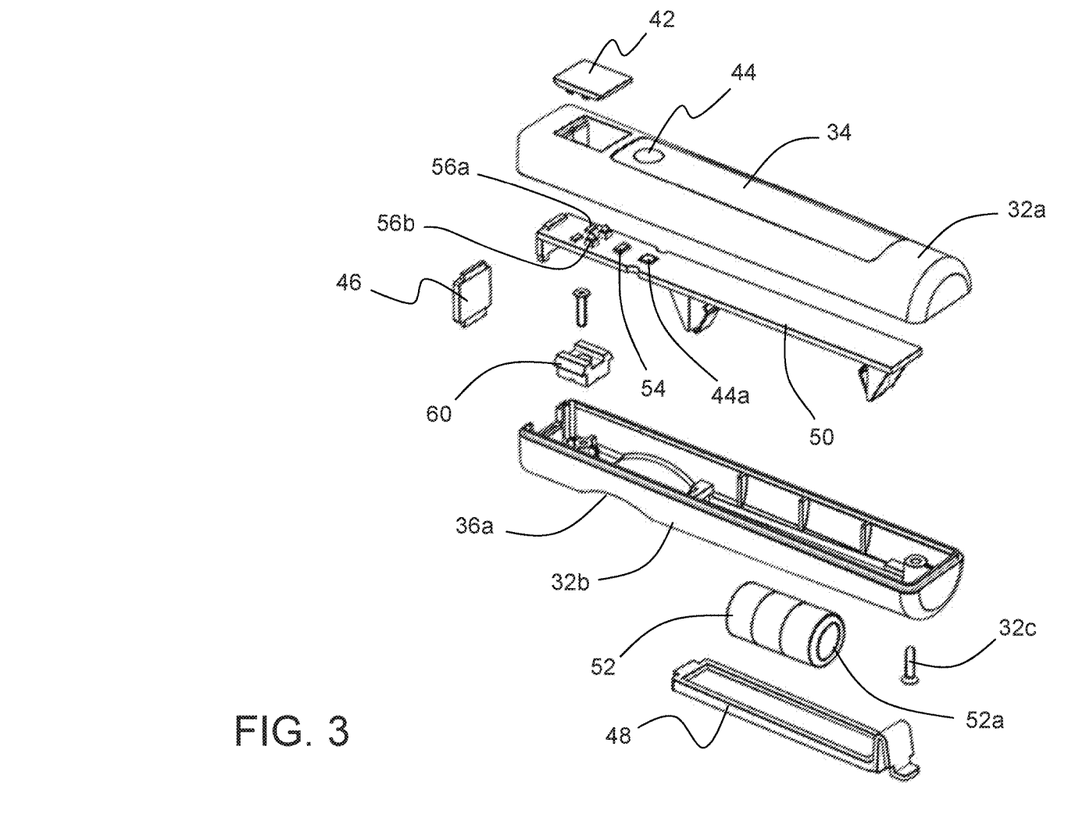
FIG. 3 is an exploded perspective view of a transillumination device of the present invention having a second preferred power supply.
Figure 4:
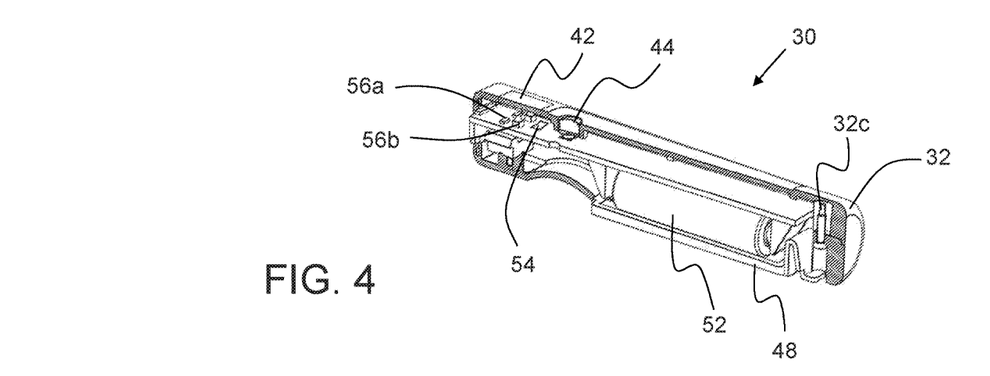
FIG. 4 is a longitudinal cut-away perspective view of a transillumination device of the present invention.
Figure 5:
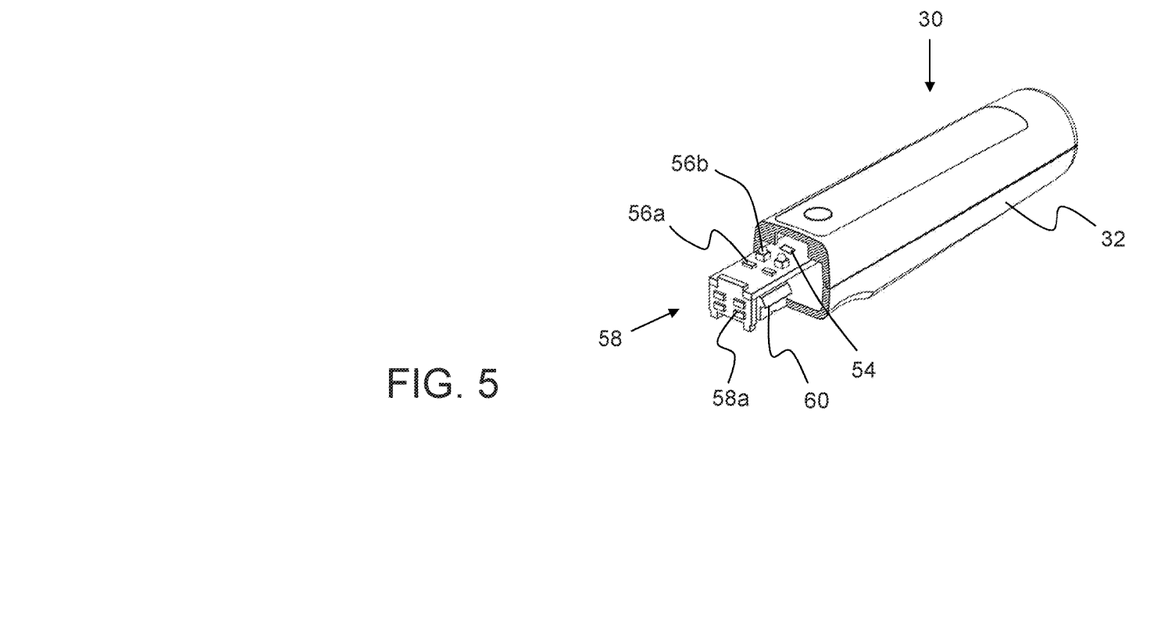
FIG. 5 is a lateral cut-away perspective view of a transillumination device of the present invention.

The device 30 has a generally elongated housing 32 split into an upper half 32a and a lower half 32b. The upper half 32a has a top longitudinal surface 34 and the bottom half 32b has a bottom longitudinal surface 36, which is generally flat or planar. The bottom half 32b preferably also includes an ergonomic finger groove 36a disposed proximate to the front of the device 30. When the halves 32a, 32b are joined, the housing 32 also has a front lateral surface 38 and a rear lateral surface 40. The halves 32a, 32b may be joined by screws 32c or other similar securing mechanisms.

Figure 1B:
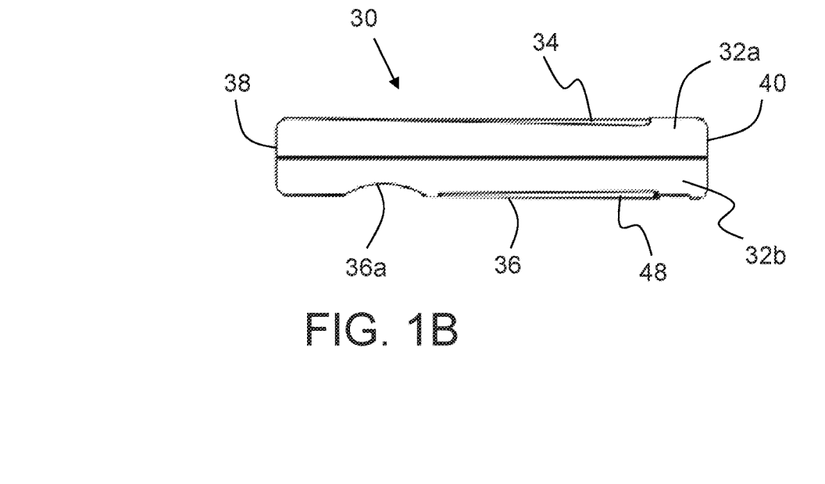
FIG. 1B is a side view of a transillumination device of the present invention.

The top longitudinal surface 34 is opaque and includes a top translucent light cover 42 and a control button 44. The top translucent light cover 42 is preferably flat and flush with the top longitudinal surface 34 as shown in FIGS. 1 and 1B.

Figure 1C:
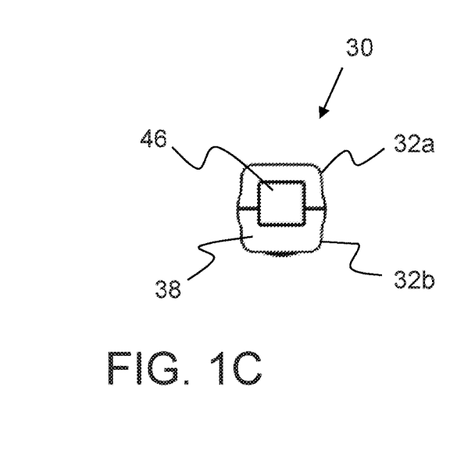
FIG. 1C is a front view of a transillumination device of the present invention.

The front lateral surface 38 is opaque and includes a front translucent cover 46. The front translucent light cover 46 is preferably flat and flush with the front lateral surface 38 as shown in FIGS. 1B and 1C. The bottom longitudinal surface 36 includes a removable cover 48.

The housing 32 encloses a circuit board 50 that includes a power supply 52, a control button contact 44a, an LED driver 54, a plurality of upward facing LEDs 56, and a plurality of forward facing LEDs 58. The power supply 52 is operationally connected to the LED driver 54, which is in turn operationally connected to each of the control button contact 44a, the upward facing LEDs 56, and the forward facing LEDs 58. The power supply 52 may include a single battery 52a or multiple batteries 52b arranged in series, which are preferably removably disposed behind the removable cover 48. A support bracket 60 may be disposed under the circuit board 30 proximate to the front of the device 10 to provide balance and support with respect to the power supply 32.

Figure 7:
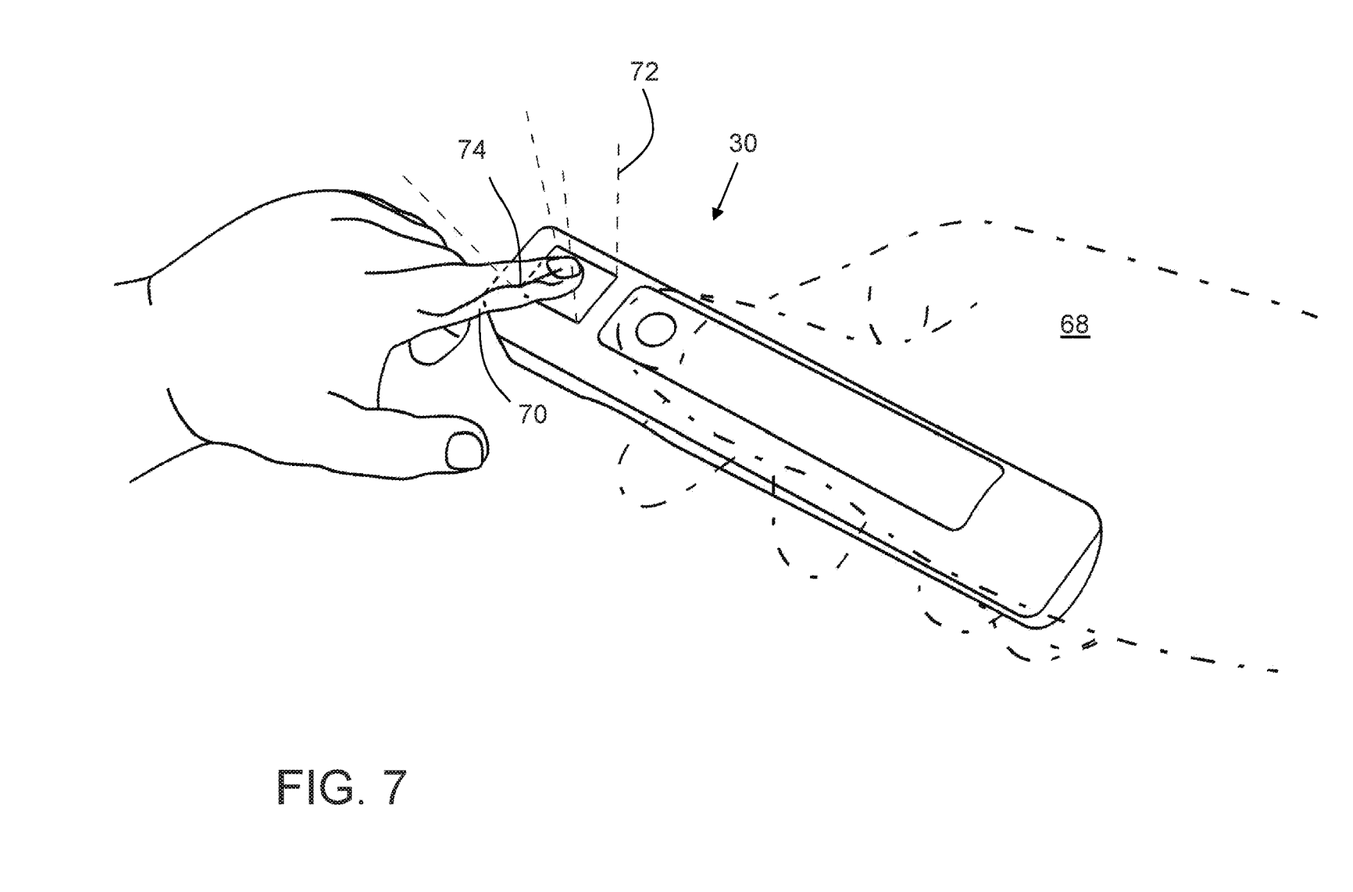
FIG. 7 is an environmental view of a transillumination device of the present invention illuminating a patient's finger.

The plurality of upward facing LEDs 56 are preferably disposed behind the first translucent light cover 42 such that light emitted by the upward facing LEDs 56 is directed upward only through the first translucent light cover 42 and illustrated in FIG. 7. The upward facing LEDs 56 preferably include at least two white LEDs 56a and at least two red LEDs 56b. Alternatively, the upward facing LEDs 56 might include multiple quantities of other color LEDs or even other light sources.

Figure 8:
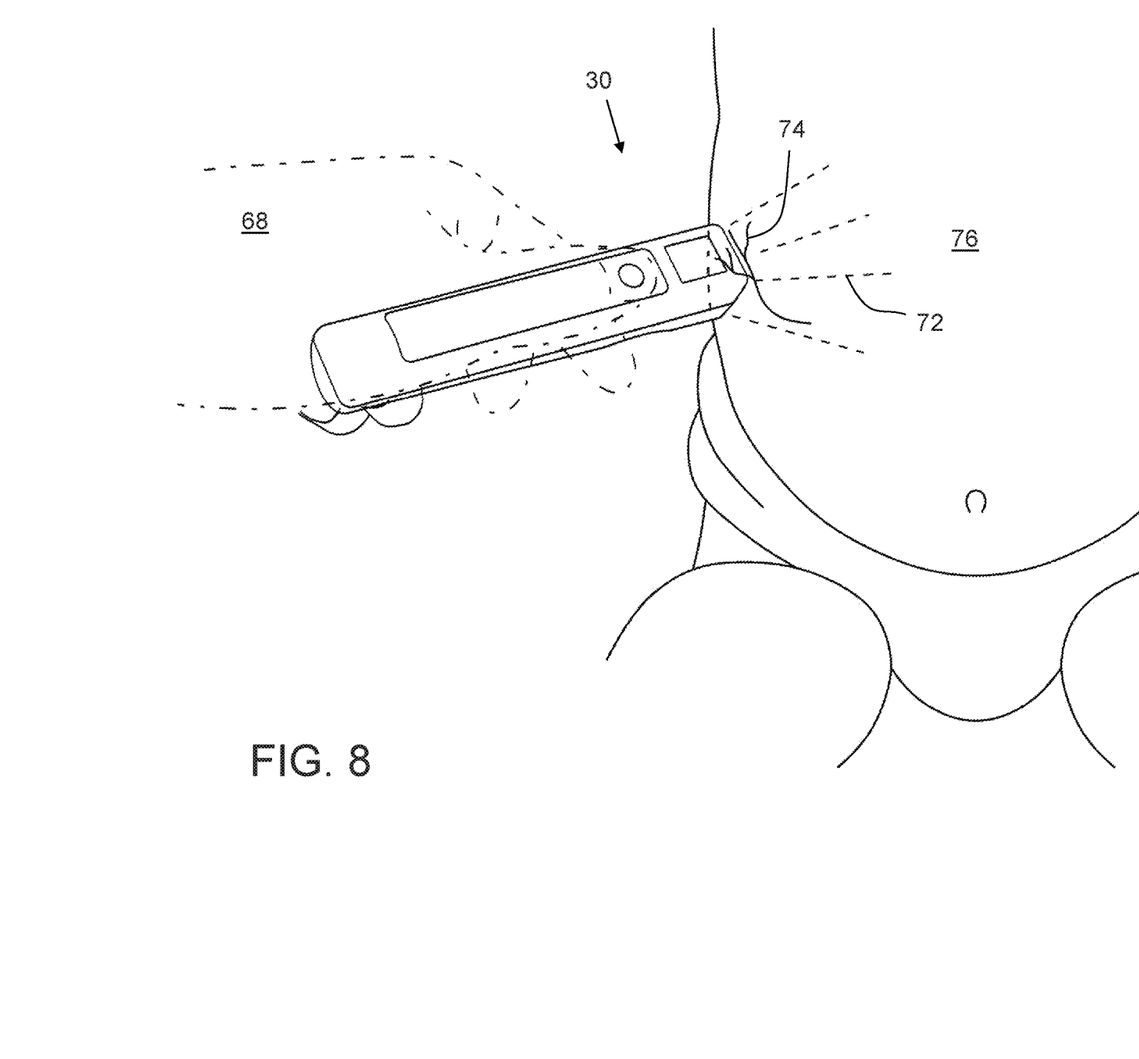
FIG. 8 is an environmental view of a transillumination device of the present invention illuminating a patient's torso.

The plurality of forward facing LEDs 58 are preferably disposed behind the second translucent light cover 46 such that light emitted by the forward facing LEDs 58 is directed forward only through the second translucent light cover 46 as illustrated in FIG. 8. The forward facing LEDs 58 preferably include four white LEDs 58a but may include other combinations or quantities of colors.

Figure 6:
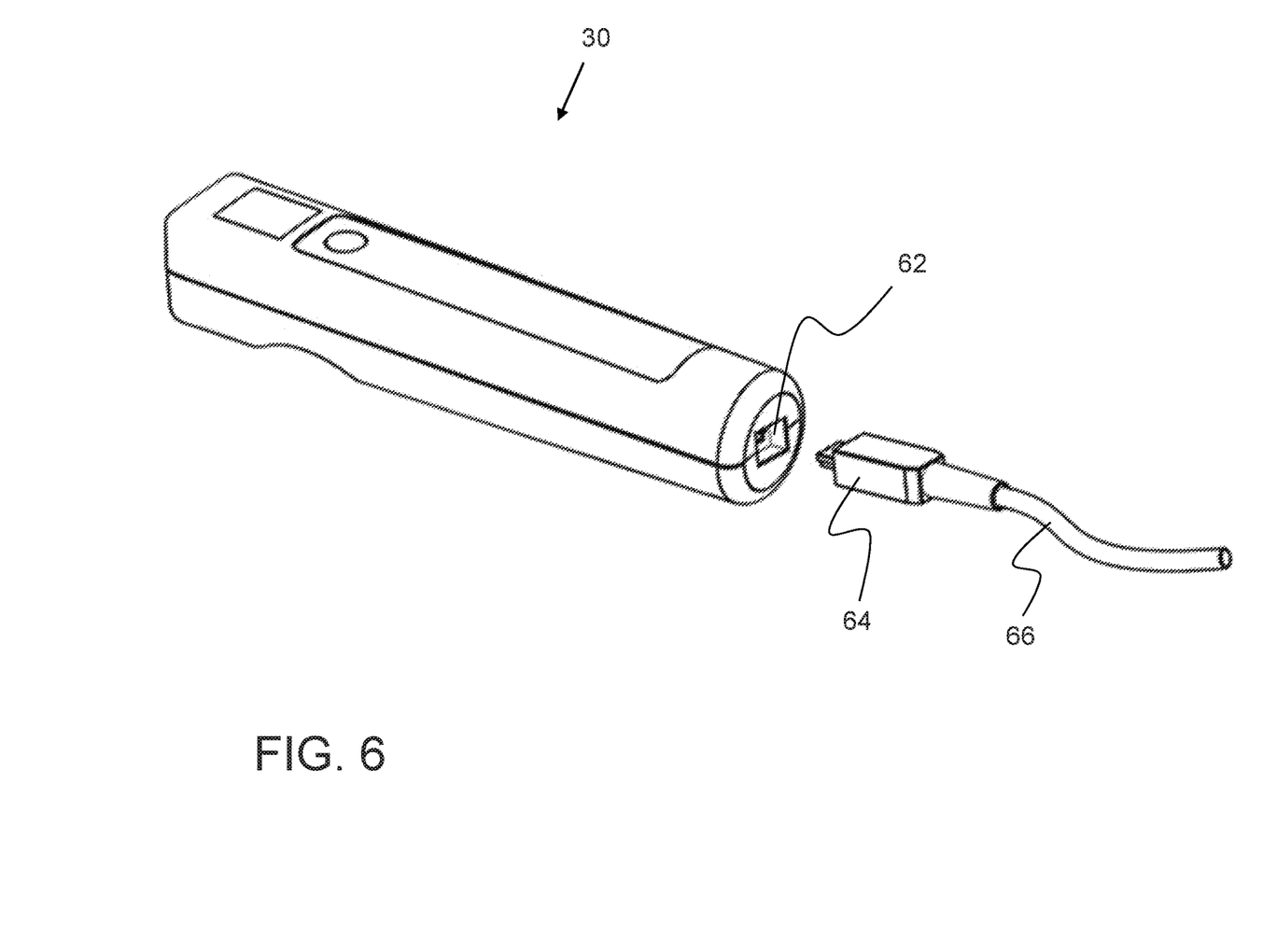
FIG. 6 is a perspective view of a transillumination device of the present invention having a third preferred power supply.

FIG. 6 illustrates an alternate embodiment where the rear lateral surface 40 includes a connection port 62 configured to receive a cable/wire 64. The cable/wire 64 is an external power source 46 in that the other end (not shown) of the cable/wire 64 is connected to a source of electricity (not shown) by commonly known devices. Typical devices might include a USB port or a power converter as may be plugged into an electrical outlet. The external power source 66 may be used to supply operating power to the device 30. Alternatively, the external power source 66 may be used to recharge a battery 52a that is rechargeable. To maintain the benefit of a freely mobile, handheld device 30, the device 30 is more preferably operated without the cable/wire 64 plugged into the connection port 62.

The device 30 is intended to be used in a manner similar to how prior art transillumination devices are used. Namely, to illuminate extremities or larger body part to locate internal organs or subcutaneous structures, in particular blood vessels. The control button 44 may function so that when it is pressed the device 30 will switch between the different operational settings and varying intensities similar to what has already been described. For example, when the control button 44 is first pressed, the two upward facing white LEDs 56a are illuminated at a low intensity. Pressed successive times and the two upward facing white LEDs 56a are illuminated at a medium intensity and then a high intensity. Pressed again, the two upward facing white LEDs 56a are turned off and the two upward facing red LEDs 56b are illuminated at a low intensity, then a medium intensity and a high intensity when pressed successive times. Alternatively, the control button 44 may be split into two sections such that when the top half of the button 44 is pushed, the device 30 is switched between the different LEDs 56a, 56b and when the bottom half of the button 44 is pushed, the device 30 is switched between the different intensity settings. The forward facing white LEDs 58a would operate in a similar manner when the button 44 is pressed additional times.

As shown in FIG. 7, the device 30 may be easily and conveniently hand-held as by a practitioner 68. An extremity of a patient, as a finger 70, is positioned over the top translucent light panel 42 and illuminated by the light 72 emitted by one or more of the plurality of upward facing LEDs 56. As the light 72 emitted passes through the finger 70, one or more internal structures, e.g., blood vessels 74, are made visible through the skin of the finger 70.

With the device 30 constructed as described above, the use the same to transilluminate a finger 70 or other extremity can be simplified for a practitioner 68 insofar as the generally flat, planar bottom longitudinal surface 36 may be rested on a working surface as a table or other accessible surface (not shown). The finger 70 or other extremity of the patient may then be laid across the top translucent light panel 42 without the need for the practitioner to hold the device 10. This functionality frees up both of the practitioner's hands to manipulate the finger 70 or other extremity and perform the applicable procedure, e.g., drawing blood or installing an IV line. Because of the relatively narrow width of fingers or other extremities, the upward facing LEDs 56 may be provided with two or more LEDs of the same color because of lower intensity of light is needed to reveal internal structures.

In FIG. 8, an alternate use of the device 30 is shown. In this instance a practitioner 68 needs to transilluminate a patient's torso 76. The practitioner 68 holds the front translucent light panel 46 against the patient's torso 76 so that light 72 emitted by the forward facing LEDs 58 passes through the skin and illuminates blood vessels 74 or other structure in the torso 76. Given the thickness and/or density of internal structures in a torso 76, the forward facing LEDs 58 are preferably provided with four or more LEDs to provide a greater intensity of light.

Figure 9:
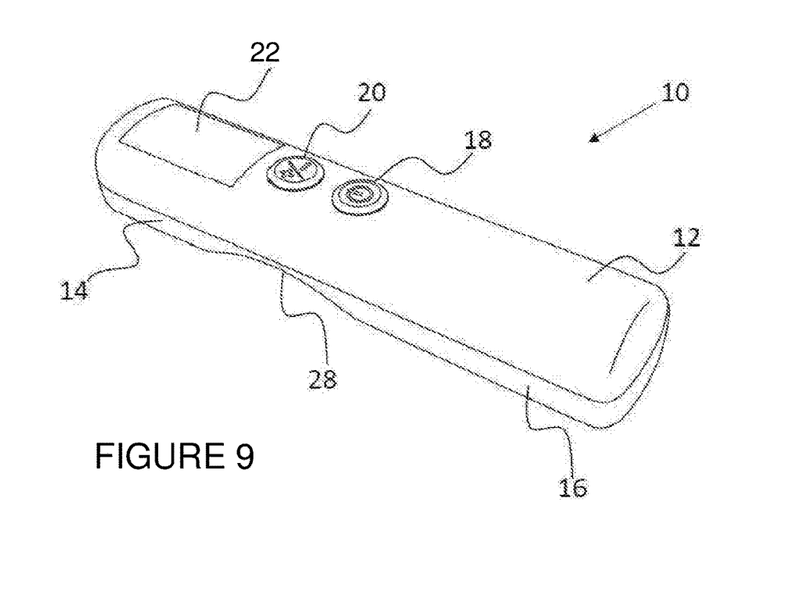
FIG. 9 is a perspective view of an alternate embodiment of a transillumination device of the present invention.

FIG. 9 illustrates an alternate embodiment of the transillumination device 10. This embodiment 10 is substantially similar to the form described above, including an upper housing 12, a lower housing 14, a battery cover 16, a top translucent light cover 22, and a finger indentation 28. The primary distinction is in the configuration of the control button. In this embodiment 10, the control button is provided as a separate power button 18 and a separate light intensity button 20.

The power button 18 and a light intensity button 20 extend through two apertures in the upper housing 12. The power button 12 functions to turn the device 10 on and off as well as to switch between various illumination modes, similar to the operational settings described above. The light intensity button 20 functions to increase and decrease the intensity of the light emitted by the device 10. The power button 18 and the light intensity button 20 may be hard plastic push buttons, rubber push buttons, or any other type of button known in the art.

Figure 10:
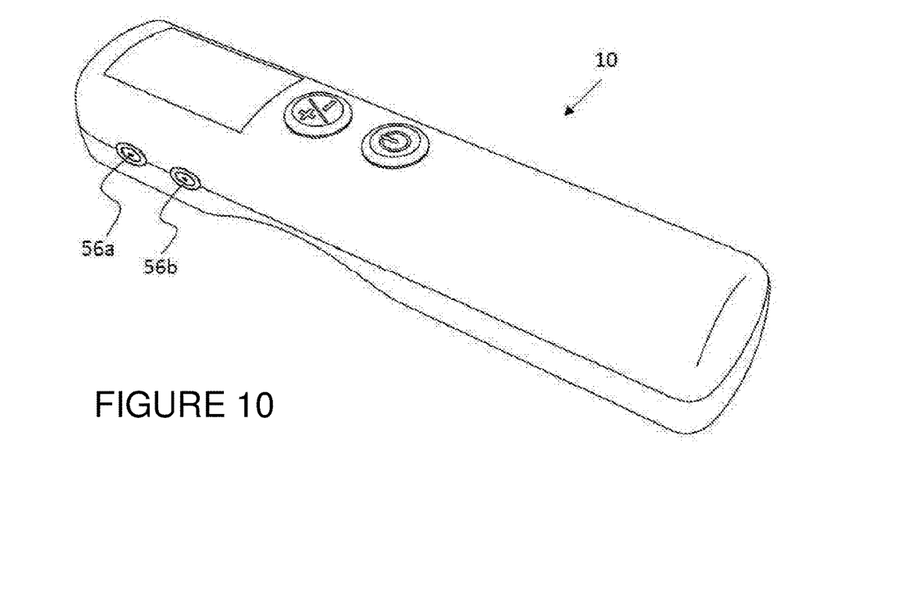
FIG. 10 is a perspective view of an alternate embodiment of a transillumination device of the present invention.
Figure 11:
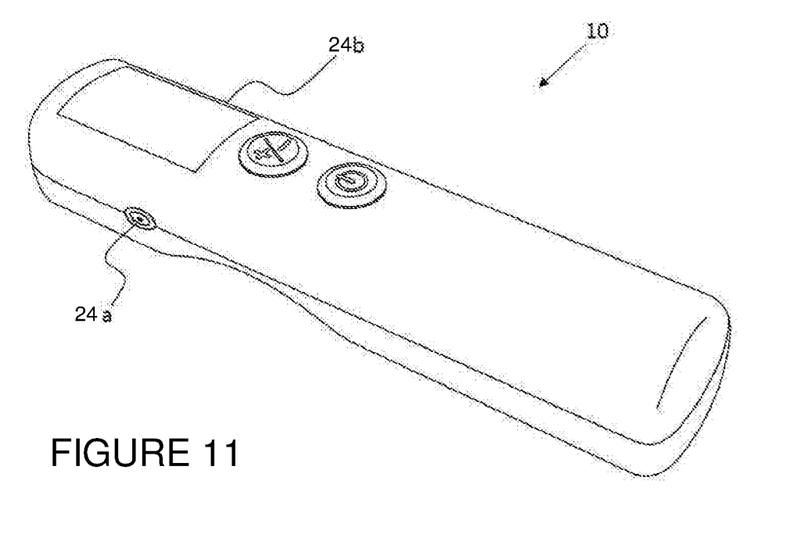
FIG. 11 is a perspective view of an alternate embodiment of a transillumination device of the present invention.

FIG. 10 illustrates another alternate embodiment where the light intensity button 20 may be supplemented by intensity touch sensors 24a, 24b on the side of the device 10 so as to be operable by a single finger. The intensity touch sensors 24a, 24b operate similar to the intensity settings discussed above. The intensity touch sensors 24a, 24b may also replace the light intensity button 20 entirely. In another alternative embodiment, shown in FIG. 11, the intensity touch sensors 24a, 24b may be presented on opposite sides of the device 10 so as to be operable by a thumb and finger.

Figure 12:
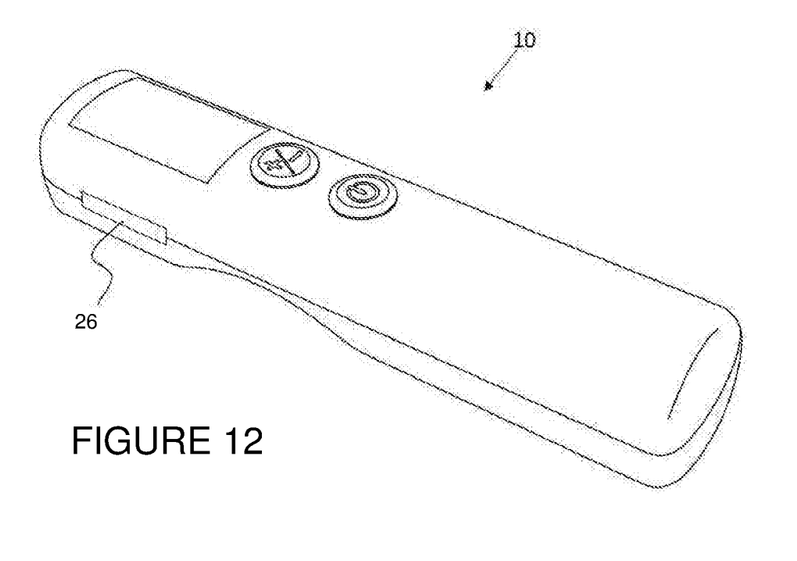
FIG. 12 is a perspective view of an alternate embodiment of a transillumination device of the present invention.

FIG. 12 illustrates that the transillumination light source 10 may alternatively include a brightness intensity touch strip 26 rather than the light touch sensors 24a, 24b. The touch strip 26 functions to steadily increase or decrease the brightness intensity, preferably from a range of 20% to 100%. However, this range may extend from the LEDs being off to being at 100% intensity. When a clinician's finger is rubbed forward on the brightness intensity touch strip 58, the brightness intensity of the LEDs will steadily increase to a maximum of 100%. Conversely, when a clinician's finger is rubbed backwards on the brightness intensity touch strip 26 the brightness intensity of the LEDs will preferably steadily decrease to a minimum of 20%, but may decrease until the LEDs are off.

Figure 13:
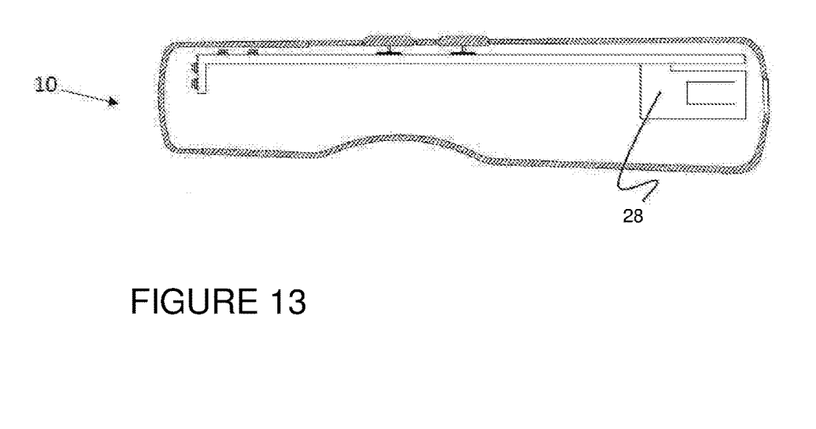
FIG. 13 is a cross-sectional view of an alternate embodiment of a transillumination device of the present invention.

FIG. 13 illustrates an alternative embodiment for introducing power to the circuit board 50. In conjunction with FIG. 6, this embodiment includes a USB-port connection 28 or similar means of receiving the cable/wire 64. This USB-port connection 28 may be connected to a lithium-ion battery or similarly rechargeable storage cell.

Although several embodiments have been described in detail for purposes of illustration, various modifications may be made without departing from the scope and spirit of the invention. Accordingly, the invention is not to be limited, except as by the appended claims.

What is claimed is:

1. A transillumination light source, comprising:
   an opaque housing having a top longitudinal surface, a bottom longitudinal surface, and a front lateral surface, wherein the bottom longitudinal surface has a generally flat portion configured to rest the housing on a flat work surface, wherein the top longitudinal surface is generally opposite the bottom longitudinal surface and has a first translucent light cover that is flat and flush with the top longitudinal surface, wherein the front lateral surface is oriented generally perpendicular to the bottom longitudinal surface and has a second translucent light cover that is flat and flush with the front lateral surface;
   a circuit board contained within the housing, wherein the circuit board carries a power supply, an LED driver, and a control button, all operationally connected to each other;
   a plurality of upward facing LEDs disposed on the circuit board behind the first translucent light cover, operationally connected to the LED driver, and configured so as to direct illumination upward only through the first translucent light cover; and
   a plurality of forward facing LEDs disposed on the circuit board behind the second translucent light cover, operationally connected to the LED driver, and configured so as to direct illumination forward only through the second translucent light cover.

2. The transillumination light source of claim 1, wherein the plurality of upward facing LEDS comprise two white LEDs.

3. The transillumination light source of claim 2, wherein the plurality of upward facing LEDs further comprise two red LEDs.

4. The transillumination light source of claim 1, wherein the plurality of forward facing LEDs comprise four white LEDs.

5. The transillumination light source of claim 3, wherein the control button has an operational setting configured to operate the LED driver to illuminate only the two white LEDs in the plurality of upward facing LEDs.

6. The transillumination light source of claim 3, wherein the control button has an operational setting configured to operate the LED driver to illuminate only the two red LEDs in the plurality of upward facing LEDs.

7. The transillumination light source of claim 4, wherein the control button has an operational setting configured to operate the LED driver to illuminate only the four white LEDs in the plurality of forward facing LEDs.

8. The transillumination light source of claim 1, wherein the control button has an intensity setting configured to regulate a brightness of LEDs illuminated by the LED driver.

9. The transillumination light source of claim 1, further comprising a connection port on the housing, wherein the connection port is operationally connected to the power supply and the transillumination light source is configured to be powered from an external source through the connection port.

10. The transillumination light source of claim 1, wherein the power supply comprises a battery enclosed behind a battery cover on the housing.

11. The transillumination light source of claim 10, wherein the battery is a rechargeable battery configured to be recharged through a connection port on the housing operationally connected to the rechargeable battery.

12. A transillumination light source, comprising:
an opaque housing having a top longitudinal surface, a bottom longitudinal surface, and a front lateral surface, wherein the bottom longitudinal surface has a generally flat portion configured to rest the housing on a flat work surface, wherein the top longitudinal surface is generally opposite the bottom longitudinal surface and has a first translucent light cover that is flat and flush with the top longitudinal surface, wherein the front lateral surface is oriented generally perpendicular to the bottom longitudinal surface and has a second translucent light cover that is flat and flush with the front lateral surface;
a circuit board contained within the housing, wherein the circuit board carries a power supply, an LED driver, and a control button, all operationally connected to each other;
a plurality of upward facing LEDs disposed on the circuit board behind the first translucent light cover, operationally connected to the LED driver, and configured so as to direct illumination upward only through the first translucent light cover, wherein the plurality of upward facing LEDs comprise two white LEDs and two red LEDs; and
a plurality of forward facing LEDs disposed on the circuit board behind the second translucent light cover, operationally connected to the LED driver, and configured so as to direct illumination forward only through the second translucent light cover, wherein the plurality of forward facing LEDs comprise four white LEDs.

13. The transillumination light source of claim 12, wherein the control button has an operational setting configured to operate the LED driver to illuminate only the two white LEDs in the plurality of upward facing LEDs.

14. The transillumination light source of claim 12, wherein the control button has an operational setting configured to operate the LED driver to illuminate only the two red LEDs in the plurality of upward facing LEDs.

15. The transillumination light source of claim 12, wherein the control button has an operational setting configured to operate the LED driver to illuminate only the four white LEDs in the plurality of forward facing LEDs.

16. The transillumination light source of claim 12, wherein the control button has an intensity setting configured to regulate a brightness of LEDs illuminated by the LED driver.

17. The transillumination light source of claim 12, further comprising a connection port on the housing, wherein the connection port is operationally connected to the power supply and the LED driver is configured to be powered from an external source through the connection port.

18. The transillumination light source of claim 12, wherein the power supply comprises a battery enclosed behind a battery cover on the housing.

19. The transillumination light source of claim 18, wherein the battery is a rechargeable battery configured to be recharged through a connection port on the housing operationally connected to the rechargeable battery.

20. A transillumination light source, comprising:
an opaque housing having a top longitudinal surface, a bottom longitudinal surface, and a front lateral surface, wherein the bottom longitudinal surface has a generally flat portion configured to rest the housing on a flat work surface, wherein the top longitudinal surface is generally opposite the bottom longitudinal surface and has a first translucent light cover that is flat and flush with the top longitudinal surface, wherein the front lateral surface is oriented generally perpendicular to the bottom longitudinal surface and has a second translucent light cover that is flat and flush with the front lateral surface;
a circuit board contained within the housing, wherein the circuit board carries a power supply, an LED driver, and a control button, all operationally connected to each other, wherein the power supply comprises a rechargeable battery enclosed behind a battery cover on the housing;
a connection port on the housing, wherein the connection port is operationally connected to the power supply and the rechargeable battery is configured to be recharged through the connection port, wherein the LED driver is configured to be selectively powered from the rechargeable battery or an external source through the connection port;
a plurality of upward facing LEDs disposed on the circuit board behind the first translucent light cover, operationally connected to the LED driver, and configured so as to direct illumination upward only through the first translucent light cover, wherein the plurality of upward facing LEDs comprise two white LEDs and two red LEDs;
a plurality of forward facing LEDs disposed on the circuit board behind the second translucent light cover, operationally connected to the LED driver, and configured so as to direct illumination forward only through the second translucent light cover, wherein the plurality of forward facing LEDs comprise four white LEDs;
wherein the control button has an operational setting configured to operate the LED driver to selectively illuminate only the two white LEDs in the plurality of upward facing LEDs, only the two red LEDs in the plurality of upward facing LEDs, or only the four white LEDs in the plurality of forward facing LEDs; and
wherein the control button has an intensity setting configured to regulate a brightness of the LEDs illuminated by the LED driver.

* * * * *